US00RE38629E1

(19) United States
(12) Reissued Patent
Bonhomme et al.

(10) Patent Number: US RE38,629 E
(45) Date of Reissued Patent: Oct. 19, 2004

(54) SOLID ORAL DOSAGE FORM COMPRISING A COMBINATION OF METFORMIN AND GLIBENCLAMIDE

(75) Inventors: Yves Bonhomme, Charbonnieres les Bains (FR); Geoffrey Nicholson, Aylesbury (GB); Gillian Cave, Flintshire (GB); Sarah J. Nicholson, Cheshire (GB)

(73) Assignee: Merck Sante, Lyons (FR)

(21) Appl. No.: 10/329,426

(22) Filed: Dec. 27, 2002

Related U.S. Patent Documents

Reissue of:
(64) Patent No.: 6,303,146
Issued: Oct. 16, 2001
Appl. No.: 09/353,141
Filed: Jul. 14, 1999

(30) Foreign Application Priority Data

Jul. 15, 1998 (EP) ..... 98401781

(51) Int. Cl.[7] ..... A61K 9/14; A61K 9/16; A61K 9/20; A61K 9/22; A61K 9/24

(52) U.S. Cl. ..... 424/465; 424/451; 424/452; 424/464; 424/465; 424/468; 424/469; 424/470; 424/489; 424/494

(58) Field of Search ..... 424/451, 452, 424/464, 465, 468, 469, 470, 489, 494

(56) References Cited

U.S. PATENT DOCUMENTS 3,174,901 A * 3/1965 Sterne
3,979,520 A * 9/1976 Rothe et al.
4,060,634 A * 11/1977 Rothe et al.
4,916,163 A * 4/1990 Ni
5,631,224 A * 5/1997 Efendic et al.
5,663,198 A * 9/1997 Reul et al.
5,922,769 A * 7/1999 Barelli et al.
5,965,584 A * 10/1999 Ikeda et al.
6,544,564 B1 * 4/2003 Farley ..... 424/729

FOREIGN PATENT DOCUMENTS

| | | | |
|---|---|---|---|
| AU | A-42302/89 | * | 4/1990 |
| DE | 0 362 704 | * | 4/1990 |
| WO | WO 97/17975 | * | 5/1997 |
| WO | WO 98/57634 | * | 12/1998 |

OTHER PUBLICATIONS

R. Vigneri, et al., Diabete & Metabolisme, vol. 17, pp. 232–234, "Treatment of NIDDM Patients With Secondary Failure to Glyburide: Comparison of the Addition of Either Metformin or Bed–Time NPH Insulin to Glyburide", 1991.*

Linda Higginbotham, et al., The Medical Journal of Australia, pp. 154–156, "Double–Blind Trail of Metformin in the Therapy of Non–Ketotic Diabetics", Aug. 11, 1979.*

Iris J. Edwards, et al., Diabetes, vol. 46, No. 5, Suppl. 1, pp. 45A, "Combination Glipizide Gits/Metformin Treatment Reduces Low Density Lipoprotein Binding To Arterial Proteoglycanes In NIDDM", 1997.*

William T. Cefalu, et al., Diabetes, vol. 45, Suppl. 2, pp. 201A, "Combination Glipizide Gits/Metformin Normalizes Glucose And Improves Insulin Sensitivity In Hyperinsulinemic Moderately Well Controlled NIDDM", 1996.*

(List continued on next page.)

*Primary Examiner*—Thurman K. Page
*Assistant Examiner*—S. Tran
(74) *Attorney, Agent, or Firm*—Millen, White, Zelano & Branigan, P.C.

(57) ABSTRACT

The present invention relates to a solid oral dosage form comprising a combination of metformin and glibenclamide in which the size of glibenclamide is such that the glibenclamide bioavailability is comparable to the glibenclamide bioavailability obtained with a separate administration of metformin and glibenclamide.

35 Claims, 3 Drawing Sheets

OTHER PUBLICATIONS

Figure 1:
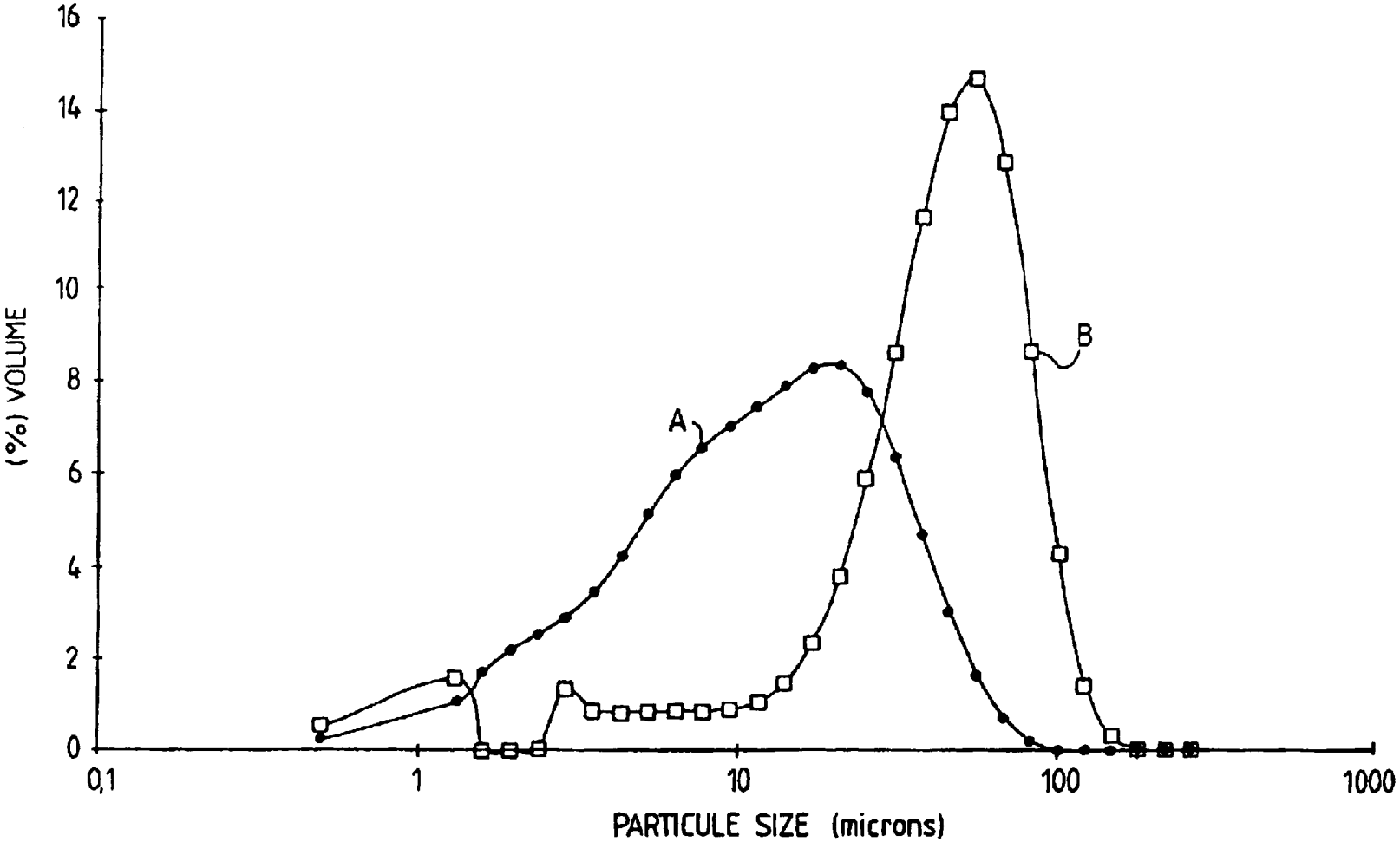

John R. Crouse, et al., Circulation, vol. 94, No. 8, Suppl. 1508, Effects Of Combination Glipizide Gits/Metformin Treatment on Oxidizability Of LDL In Non–Insulin Dependent Diabetes Mellitus, 1996.*

W. T. Cefalu, et al., Diabetologia, vol. 39, Suppl. 1, pp. A231, "Insulin Sensitivity Is Improved After Glipizide Monotherapy And Combination With Metformin", 1996.*

Gerald M. Reaven, et al., Journal of Clinical Endocrinology and Metabolism, vol. 74, No. 5, pp. 1020–1026, Combined Metformin–Sulfonylurea Treatment Of Patients With Non–insulin–Dependent Diabetes In Fair To Poor Glycemic Control, 1992.*

Bi–Euglucon M Italian Package Insert, Repenono Farmaceutco Italiano, 1998 (with English translation pp. 1–9).*

CB Hollenbeck, et al., Diabetes, vol. 39, Suppl. 1, pp. 108A, "Combination Glipizide/Metformin Treatment In Non–Insulin Dependent Diabetes (NIDDM)", 1990.*

Press Release Sep. 30, 1999: Bristol–Myers Squibb Files New Drug Application for Novel Oral Antidiabetic Drug, 2 pp., 1999.*

Glucomide—Italian Package Insert, Repertorio Farmaceutico Italiano, 1 p., 1999 (with English translaction pp. 1–6).*

Glibomet—Italian Package Insert, Repertorio Farmaceutico Italiano, 1 p., 1999 (with English translation pp. 1–7).*

Suguan M—Italian Package Insert, Repertorio Farmaceutico Italiano, 1 p., 1999 (with English translation pp. 1–9).*

Blume et al., Drug Development and Industrial Pharmacy, 19(20), 2713–2741 (1993).

PDR, 56 ed, 2002, "Alyburide" listing and Glucophage ® and Glucovance ® package inserts.

PDR, 52 ed, 1998, "Glyburide" listing, generic listings and Micronase®, Glynase® and Dia Beta® package inserts.

AU 42302/89 Abstract.

Al–Ahmed et al., "Bioscience Reports," vol. 9, No. 3, 1989, 347–350.

Letter dated Apr. 1, 2002 from Ivax Pharmaceuticals, Inc. to Lipha, S.A. (assignee of U.S. Pat. No. 6,303,146) and Bristol–Myers Squibb (marketer of Clucovance® covered by U.S. Pat. No. 6,303,146).

* cited by examiner

SOLID ORAL DOSAGE FORM COMPRISING A COMBINATION OF METFORMIN AND GLIBENCLAMIDE

Matter enclosed in heavy brackets [ ] appears in the original patent but forms no part of this reissue specification; matter printed in italics indicates the additions made by reissue.

The present invention relates to solid oral dosage forms for the treatment of non-insulin dependent diabetes.

Non-insulin dependent diabetes is a metabolic disorder characterized by hyperglycaemia, which occurs due to insulin deficiency, insulin resistance and reduced glucose tolerance.

There are two main groups of oral antidiabetic drugs available: these are the sulphonylureas and the biguanidines. Sulphonylureas act by stimulating insulin release and are thus only effective with some residual pancreatic beta-cell activity, examples of sulphonylureas available are glibenclamide, gliclazide, tolbutamide, glipizide, tolazamide, gliquidone and chlorpropamide. The biguanidines, such as metformin, act by decreasing gluconeogenesis and by increasing peripheral utilisation of glucose, and as they require endogenous insulin they are only effective with some residual pancreatic islet cell activity.

The initial treatment of non-insulin dependent diabetes involves diet control and exercise. Only after this has been shown to be inadequate are oral antidiabetic drugs used, and then only to complement the effect of diet and not replace it. Monotherapy with an oral antidiabetic can be an effective treatment for many years. However the efficiency can decrease with time. Due to sulphonylureas and biguanidines having complementary modes of action, combined therapy is now an established form of treatment for non-insulin dependent diabetes.

To improve patient compliance a combined tablet would be an advantage. The present invention relates to solid oral dosage forms comprising a combination of mefformin and glibenclamide (also named glyburide).

A combination of metformin with glibenclamide has been disclosed in WO 97/17975 for the treatment of type II diabetes with a defined ratio of the two active ingredients, which is a requirement in order to obtain an optimum therapeutic effect. This prior art defines an optimum therapeutic ratio of metformin hydrochloride to glibenclamide of 100:1, for example 500 mg of metformin hydrochloride with 5 mg glibenclamide in a single dosage unit. This ratio allows a range of daily doses, based on increasing the number of tablets taken per day, that avoid poor disease control through underdosing of either ingredient when there is a requirement for co-administration, and avoids hypoglycaemia by overdosing of either component when so co-administered. Assurance of performance in clinical use, which will derive from having a product exhibiting appropriate bioavailability of the glibenclamide component, is a key requirement for physicians wishing to treat patients with a combination formulation. Appropriate bioavailability implies that 5 mg of glibenclamide formulated into a combination tablet with metformin is absorbed to an acceptably similar extent, and at a comparable rate, to glibenclamide dosed as a single entity formulation of the same strength when dosed concurrently with a single entity formulation of metformin.

This prior art does not teach how to formulate a combination product of metformin with glibenclamide so as to assure appropriate bioavailability of the glibenclamide component. There is no issue in this respect in the case of metformin hydrochloride on account of its high water solubility and therefore the bioavailability of metformin from combination formulations will not be discussed further. It is however a very important aspect to consider for glibenclamide as this is a poorly soluble drug substance (solubility is 0.1 mg/ml in water at 25° C.—practically insoluble as defined by the USP).

As such, its rate of solution after administration of a dosage form will influence the rate and extent of entry of the drug into the bloodstream (bioavailability). The control of the rate and extent of entry into the bloodstream is important for appropriate therapeutic effect.

Hence, the reference discloses a suitable ratio of the two active ingredients in a single dosage form, in order to model how the two individual ingredients might be desirably co-administered (based on how they would be dosed according to usual practice associated with currently available single entity formulations), it does not teach how to assure that such a combination formulation will perform in terms of bioavailability of glibenclamide. This bioavailability should be as similar as possible to when the relevant doses of the two single entity formulations are co-administered.

In addition, when a combination tablet using standard galenic procedures is proceeded with standard generic glibenclamide in the combination tablet, a reduced bioavailability in comparison to the co-prescribed situation was apparent.

It has now been found using in-vitro and in-vivo testing that the reduced bioavailability is related to the particle size and the particle size distribution of the glibenclamide. It has been found that particles which are too small result in high glibenclamide blood levels with consequent risk of hypoglycaemia and particles which are too large cannot dissolve sufficiently rapidly to give comparable bioavailability with the co-prescribed situation. It is therefore necessary to have a closely defined particle size distribution of the glibenclamide in the combination form.

The selection of a specific size fraction of glibenclamide enables the production of a solid oral dosage form comprising a combination of metformin and glibenclamide, and in particular a tablet, exhibiting glibenclamide bioavailability comparable to the bioavailability obtained with the separated administration of metformin and glibenclamide, when judged by the area under the curve of the in-vivo analysis.

The present invention provides in particular a tablet comprising a combination of metformin and glibenclamide, exhibiting a comparable glibenclamide bioavailability to the co-administered tablets.

In a first embodiment, the solid oral form such as a tablet, according to the invention, contains a combination of glibenclamide and metformin in which the size of the glibenclamide is such that at most 10% of the particles are less than 2 $\mu$m and at most 10% of the particles are greater than 60 $\mu$m. Preferably, the size of the glibenclamide is such that at most 10% of the particles are less than 3 $\mu$m and at most 10% of the particles are greater than 40 $\mu$m. This specific particle size range of glibenclamide may be obtained by sieving or air jet milling.

In a second embodiment, the solid oral dosage form comprises a combination of metformin and glibenclamide in which the size of glibenclamide is such that at most 25% of the particles are less than 11 $\mu$m and at most 25% of the particles are greater than 46 $\mu$m.

Preferably, 50% of particles are less than 23 $\mu$m.

Metformin may be used as a salt of metformin, such as hydrochloride, fumarate, hydrobromide, p-chlorophenoxy acetate or embonate. The weight ratio of metformin salt to glibenclamide should preferably be between 50/1 to 250/1.

The preferred compositions for the oral dosage form is provided in the table below, with ranges on components being provided:

| Ingredient | Amount of ingredient, mg per tablet Product identity | | |
|---|---|---|---|
| | 500/5 | 500/2.5 | 250/1.25 |
| Metformin hydrochloride | 500.0 | 500.0 | 250.0 |
| Glibenclamide | 5.00 | 2.50 | 1.25 |
| Croscarmellose sodium | 6.0–30.0 | 6.0–30.0 | 3.0–15.0 |
| Microcrystalline cellulose | 30.0–120.0 | 30.0–120.0 | 15.0–60.0 |
| Polyvinyl pyrrolidone | 6.0–36.0 | 6.0–36.0 | 3.0–18.0 |
| Magnesium stearate | 0.6–15.0 | 0.6–15.0 | 0.3–7.5 |
| Film coat* | 9.0–24.0 | 9.0–24.0 | 4.5–12.0 |

*a commercially-available film coat composition is used, such as Opadry (Colorcon, UK).

The especially preferred compositions are as follows:

| Ingredient | Amount of ingredient, mg per tablet Product identity | | |
|---|---|---|---|
| | 500/5 | 500/2.5 | 250/1.25 |
| Metformin hydrochloride | 500.0 | 500.0 | 250.0 |
| Glibenclamide | 5.00 | 2.50 | 1.25 |
| Croscarmellose sodium | 14.0 | 14.0 | 7.0 |
| Microcrystalline cellulose | 54.0 | 56.5 | 28.25 |
| Polyvinyl pyrrolidone | 20.0 | 20.0 | 10.0 |
| Magnesium stearate | 1.2–12.0 | 1.2–12.0 | 0.6–6.0 |
| Film coat* | 9.0–24.0 | 9.0–24.0 | 4.5–12.0 |

*a commercially-available film coat composition is used, such as Opadry (Colorcon, UK).

The tablet according to the present invention may be obtained by a process comprising:

a) forming granules by wet granulation of a mixture of metformin and glibenclamide;

b) blending the granules with a tabletting aid and diluent, and c) tabletting the blend thus obtained into tablets.

Advantageously the mixture used for forming the granules comprises a granulating binder. This granulating binder is in particular a polyvinylpyrolidone such as for example, a polyvinylpyrolidone having a molecular weight of 45000. The polyvinylpyrolidone may be used in a proportion of 2 to 4% by weight with respect to the final tablet.

After the granulating step the granules may be sieved and dried.

The granules are then blended with a diluent and tabletting aid. The diluent may be any material usually used for making tablets, such as microcrystalline cellulose. The tabletting aid may be any material usually for making tablets, such as magnesium stearate.

The tablets thus obtained may then be coated with a hydrophilic cellulose polymer and talc. The hydrophilic cellulose polymer may be 2-hydroxypropyl methylcellulose.

The following examples and tests illustrate the present invention.

EXAMPLE 1

A tablet of metformin/glibenclamide has been prepared as follows:

66.6 g of polyvinylpyrolidone are mixed with 246 g of purified water with a stirrer. 1500 g metformin hydrochloride, 7.5 g of glibenclamide (with a 10 to 90% size range between 2 to 60 $\mu$m), 42 g croscarmellose sodium and 284.4 g of microcrystalline cellulose are mixed in a granulator. The polyvinylpyronolidone solution is added to the granulator and the wet mass is granulated. The granules are extruded through a 1 mm mesh. The granules are emptied into a preheated fluidised bed dryer and the granules are dried. 97.5 g of microcrystalline cellulose is mixed into the granules using a tumbling mixer. 12 g of magnesium stearate is added to the tumbling mixer and mix. The granule mix is tabletted using a suitable tablet press. The tablets are coated with a 2% hydroxypropyl methylcellulose coat in a coating machine.

EXAMPLE 2

A tablet of metformin/glibenclamide has been prepared as follows:

5.83 g of glibenclamide (with a 10 to 90% size range between 2 to 60 $\mu$m), are preblended with 32.67 g of croscarmellose sodium. 46.67 g of polyvinylpyrolidone are mixed with 93.33 g of purified water with a stirrer. The glibenclamide-croscarmellose sodium blend is mixed with 1166.6 g of metformin hydrochloride in a granulator. The polyvinylpyrolidone solution is added to the granulator and the wet mass is granulated. The granules are emptied into a preheated fluidised bed dryer and the granules are dried. The particle size of the granules is reduced by passing through a 1 mm mesh. 131.83 g of microcrystalline cellulose are mixed into the granules in the granulator. 16.3 g of magnesium stearate are added to the granulator and mixed. The granule mix is tabletted using a suitable tablet press. The tablets are coated with a 2% hydroxypropyl methylcellulose coat in a coating machine.

Test 1

In-vivo bioavailability tests were performed with tablets prepared as disclosed in example 2, using two batches of glibenclamide. The two batches have the following 10 to 90% particle size range:

batch A: 3.47–38.08 $\mu$m batch B: 15.63–91.6 $\mu$m;

The distribution of the particle size of batches A and B are illustrated in FIG. 1.

The two batches of tablets were administered to healthy patients in comparison to co-administered glibenclamide (marketed under the trade name Daonil) and metformin hydrochloride (16 patients for each group).

Figure 2:
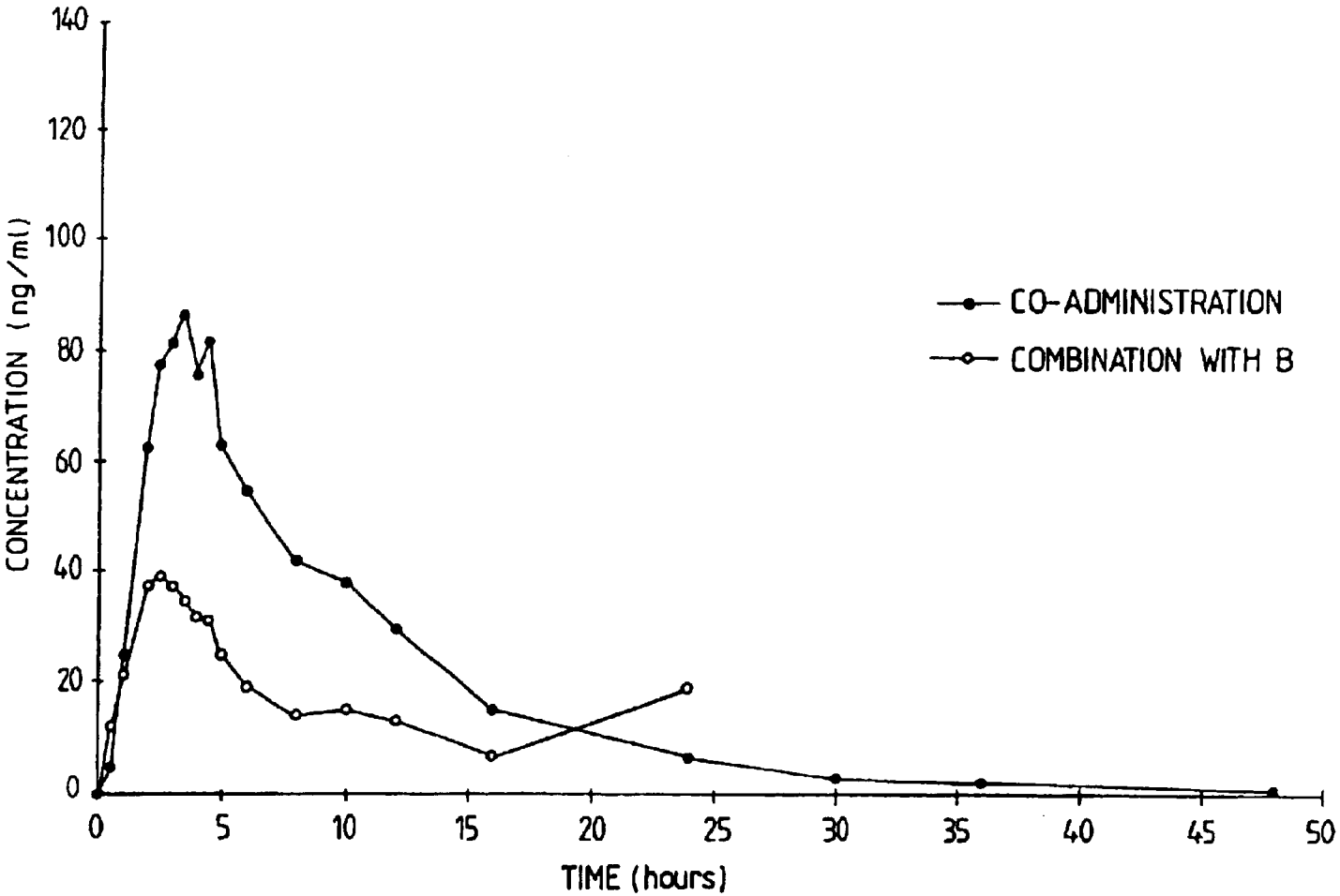
Figure 3:
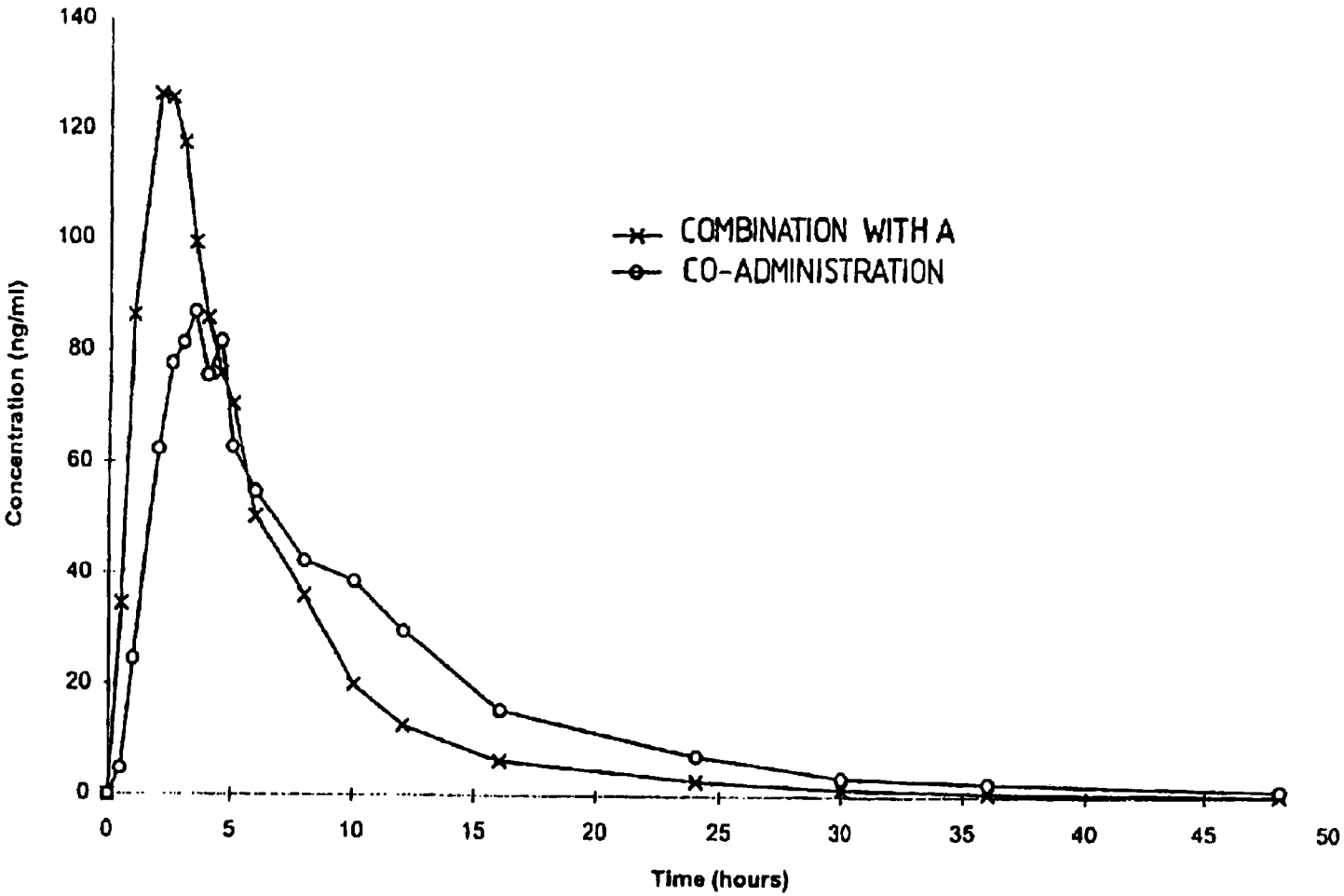

The comparative concentrations of glibenclamide in a tablet comprising a combination of metformin and respectively the batch A and the batch B of glibenclamide and with the co-administration are shown respectively in FIGS. 2 and 3.

The area under the curve (AUC) are the following:

| | AUC (ng/ml/h) |
|---|---|
| combination with batch A | 790.5 |
| combination with batch B | 353.0 |
| co-administration | 869.3 |

It appears that with the combination according to the invention with batch A the AUC is substantially the same as in the case of co-administration, whereas with the combination with batch B the AUC is more clearly different.

Test 2

Careful examination of blood levels of glibenclamide in humans following administration of a series of tablet formulations of metformin hydrochloride combined with glibenclamide (identified as formulations Combo 1, 2, 3 and 4), where the formulation are identical save for the particle size characteristics of the glibenclamide used, compared with commercially available reference formulations of metformin hydrochloride (Glucophage™, Bristol-Myers Squibb) and glibenclamide (Micronase™, Upjohn) dosed together, allowed definition of particle characteristics for glibenclamide that would assure appropriate bioavailability of the glibenclamide component from the combination formulation. This means that disease control when patients are first treated with such a combination formulation will be predictable, based on prior physician knowledge of treatments employing either single drug.

Alternatively, if patients have undergone prior stabilisation of their disease by adding treatment with a commercial product like Micronase™ to existing treatment with Glucophage™ (or vice versa), then the switch over to a more convenient treatment employing the combination in a single tablet (and where the appropriate bioavailability of he glyburide component is assured) will result in the desired level of disease control being maintained.

Data from the studies with metformin hydrochloride/glibenclamide tablets formulated with glibenclamide of different particle size characteristics allowed the development of a correlation between drug particle size and the in vivo performance. The properties of the lots of glyburide used in the series of combination tablets employed are shown in the table below:

| | glibenclamide particle size (microns) | | |
|---|---|---|---|
| Tablet batch | 25% undersize | 50% undersize | 75% undersize |
| Combo 1 | 15 | 33 | 62 |
| Combo 2 | 28 | 58 | 88 |
| Combo 3 | 10 | 25 | 52 |
| Combo 4 | 6 | 11 | 19 |

When four compositionally-identical individual batches of tablets of metformin hydrochloride-glyburide 500/2.5 mg were prepared using each of these lots of glibenclamide and dosed to humans, the following pharmacokinetic parameters were found on analysis of the glibenclamide plasma concentration-time curves:

| | Pharmacokinetic parameters glibenclamide | | | |
|---|---|---|---|---|
| Tablet batch | Cmax (ng/ml, geo. mean) | AUC (ng/ml/hr, geo. mean) | Cmax (ng/ml, arith. mean) | AUC (ng/ml/hr, arith. mean) |
| Combo 1 | 71 | 478 | 76 | 493 |
| Combo 2 | 52 | 345 | 54 | 339 |
| Combo 3 | 64 | 513 | 67 | 531 |
| Combo 4 | 88 | 642 | 93 | 716 |

A reasonable correlation can be obtained between particle size and the maximum attained geometric mean glibenclamide plasma concentration, Cmax, and also with the geometric mean area under the glibenclamide plasma concentration-time curve, AUC.

From these correlations, projected limits on particle size for glyburide that would give predicted Cmax and AUC values ±25% of a mean value for batches of the reference glibenclamide formulation, Micronase™ utilised in the in vivo studies become:

| | 25% undersize limits | 50% undersize limits | 75% undersize limits |
|---|---|---|---|
| Cmax | <0–18 microns | <0–37 microns | <0–63 microns |
| AUC | <0–11 microns | <0–25 microns | <0–46 microns |

Accommodating both Cmax and AUC requirements, the projected limits then become:

| 25% undersize limits | 50% undersize limits | 75% undersize limits |
|---|---|---|
| ≦11 microns | ≦23 microns | ≦46 microns |

Glibenclamide having these particle size characteristics have powder surface area values in the range 1.7 to 2.2 $m^2 g^{-1}$ as determined by nitrogen adsorption. Therefore material of these properties when formulated as described in this work is distinct from the material disclosed in U.S. Pat. No. 3,979,520 which required glibenclamide of powder surface area in excess of 3 $m^2 g^{-1}$ (preferably 5 to 10 $m^2 g^{-1}$) to yield appropriate glibenclamide bioavailability. The glibenclamide of particle size properties detailed in this work, when formulated as described here produces appropriate glibenclamide bioavailability in humans as described in the next test.

Test 3

A batch of metformin hydrochloride-glibenclamide tablets 500/5 mg was prepared as follows. Glibenclamide (1.0 kg) with the above defined size was tumble mixed with 2.8 kg of croscarmellose sodium and this mixture was then blended in a high shear mixer with metformin hydrochloride (100 kg) to which 0.5% by weight of magnesium stearate had been added.

This dry mix was wet granulated in a high shear mixer with 12.1 kg of an aqueous solution of povidone (containing 4 kg of povidone). The wet granules were dried in a fluid bed drier at 60° C. to a defined moisture content. The dried (loss on drying 2–3% w/w) granules were size reduced in a oscillator (1.0 mm screen aperture) then tumble mixed with 10.8 kg of microcrystalline cellulose, followed by mixing with 0.9 kg of the tablet lubricant magnesium stearate. The lubricated granules were compressed using 16 mm×8 mm capsule shaped tooling and the tablet cores were film coated (weight gain approximately 2% w/w) with the proprietary film coat material Opadry 32920 to yield the final yellow, capsule-shaped tablets. In a human pharmacokinetic study volunteer either were dosed with one of these tablets or with a treatment being one 500 mg Glucophage tablet plus one 5 mg Micronase™ tablet co-administered. Glibenclamide plasma levels following dosing were analysed and the following pharmacokinetic were found for this component:

| Treatment | Parameter | Mean | Adjusted geometric mean | Ratio of means (Point estimate) |
|---|---|---|---|---|
| Combination | Cmax | 122 | 116 | 1.14 |
| Tablet 500/5 | AUC (O-T) | 859 | 831 | 1.07 |
| Glucophate + | Cmax | 113 | 101 | — |
| Micronase | AUC (O-T) | 842 | 780 | — |

Glibenclamide bioavailability from the combination tablet is comparable to that from the reference glibenclamide formulation, Micronase™. This would thus allow patients to conveniently take one tablet of the combination product instead of two tablets of existing therapies together, without concern that low glibenclamide blood levels would result, which might occur with prior art formulations and lead to loss of control of disease.

EXAMPLE 3

Instead of compressing into tablet granulation as prepared for test 3 was filled into size 00 capsules to either provide for metformin hydrochloride/glibenclamide 500 mg/5 mg product or the 500 mg/2.5 mg product. Granulation was filled into size 1 capsules to provide the 250 mg/2.5 mg product.

These capsule exhibited acceptable physical properties and provide an alternative to the tablets. Formulations as described in WO 97/17975 could not be filled in capsules of a size acceptable to most patients because of the larger amount of excipients employed the formulations they described.

What is claimed is:

1. A solid oral dosage form comprising a combination of metformin and glibenclamide in which the size of the glibenclamide is such that at most 10% of the particles are less than 2 $\mu$m and at most 10% of the particles are greater than 60 $\mu$m, so that the glibenclamide bioavailability is comparable to the glibenclamide bioavailability obtained with a separate administration of metformin and glibenclamide.

2. A solid pharmaceutical composition comprising metformin and glibenclamide in particulate form, wherein the size of the glibenclamide particles is such that at most 10% of the particles are less than 2 $\mu$m and at most 10% of the particles are greater than 60 $\mu$m.

3. A solid oral dosage form as claimed in claim 1 in which the size of the glibenclamide is such that at most 10% of the particles are less than 3 $\mu$m and at most 10% of the particles are greater than [60] *40* $\mu$m.

4. A solid oral dosage form comprising a combination of metformin and glibenclamide in which the size of glibenclamide is such that at most 25% of the particles are less than 11 $\mu$m and at most 25% of the particles are greater than 46 $\mu$m.

5. A solid oral dosage form *of claim 4* in which 50% of particles are less than 23 $\mu$m.

6. A solid oral dosage form as claimed in claim 1 in which metformin is present as metformin salt and the weight ratio of metformin salt to glibenclamide is 50/1 to 250/1.

7. A solid oral dosage form as claimed in claim 1 which is a tablet.

8. A tablet as claimed in claim 7 which is obtained by a process comprising:

a) forming granules by wet granulation of a mixture of metformin and glibenclamide;

b) blending the granules with a tabletting aid c) tabletting the blend thus obtained into tablets.

9. A method for treating non-insulin dependent diabetes or hyperglycaemia, comprising administering to a subject in need thereof, the composition of claim 1.

10. A method for treating non-insulin dependent diabetes or hyperglycemia, comprising administering to a subject in need thereof, the composition of claim 2.

*11. A pharmaceutical composition comprising a single solid oral dosage form containing an effective dose of metformin and an effective dose of glibenclamide wherein, after oral administration thereof to a human, the bioavailability of glibenclamide is comparable to the bioavailability of glibenclamide achieved by oral administration of separate solid oral dosage forms to a human, one containing glibenclamide and the other metformin, in the same respective effective doses as in said single oral dosage form.*

*12. A pharmaceutical composition comprising a single solid oral dosage form containing an effective dose of metformin and an effective dose of glibenclamide wherein, after oral administration thereof to a human, the $C_{max}$ and AUC of glibenclamide are comparable to the $C_{max}$ and AUC of glibenclamide achieved by oral administration of separate solid oral dosage forms to a human, one containing glibenclamide and the other metformin, in the same respective effective doses as in said single oral dosage form.*

*13. A pharmaceutical composition comprising a single solid oral dosage form containing an effective dose of metformin and an effective dose of glibenclamide wherein, after oral administration thereof to a human, the $C_{max}$ and AUC of glibenclamide are ±25% of the $C_{max}$ and AUC, respectively, of the glibenclamide achieved by oral administration to a human of separate solid oral dosage forms, one containing glibenclamide and the other metformin, in the same respective effective doses as in said single oral dosage form.*

*14. A pharmaceutical composition comprising a single solid oral dosage form containing an effective dose of metformin and an effective dose of glibenclamide wherein, after oral administration thereof to a human, the mean $C_{max}$ and mean AUC values of glibenclamide are, respectively, ±25% of 113 ng/ml and ±25% of 842 ng/ml/hr, for a 5 mg unit dose of glibenclamide, or proportionally higher or lower values for higher or lower unit doses of glibenclamide, respectively.*

*15. A pharmaceutical composition comprising a single solid oral dosage form containing an effective dose of metformin and an effective dose glibenclamide wherein, after oral administration thereof to a human, the adjusted geometric mean $C_{max}$ and adjusted geometric mean AUC values of glibenclamide are, respectively, ±25% of 101 ng/ml and ±25% of 780 ng/ml/hr, for a 5 mg unit dose of glibenclamide, or proportionally higher or lower values for higher or lower unit doses of glibenclamide, respectively.*

*16. A composition of one of claims 11–15 wherein the weight ratio of metformin to glibenclamide is 50/1 to 250/1.*

*17. A composition of one of claims 11–15 wherein the weight ratio of metformin to glibenclamide is about 100/1.*

*18. A composition of one of claims 11–15 wherein the weight ratio of metformin to glibenclamide is about 200.*

*19. A composition of one of claims 11–15 wherein the unit dose of metformin is about 500 mg or about 250 mg.*

*20. A composition of claim 19 wherein the unit dose of glibenclamide is 5, 2.5 or 1.25 mg.*

*21. A composition of one of claims 11–15 in the form of a tablet or capsule.*

*22. A composition of claim 13 wherein said $C_{max}$ and AUC values of glibenclamide in said single solid oral dosage form are ±20% of said $C_{max}$ and AUC values, respectively, of glibenclamide in said separate glibenclamide solid oral dosage form.*

*23. A composition of claim 13 wherein said $C_{max}$ and AUC values of glibenclamide in said single solid oral dosage form are ±15% of said $C_{max}$ and AUC values, respectively, of glibenclamide in said separate glibenclamide solid oral dosage form.*

*24. A composition of claim 13 wherein said $C_{max}$ and AUC values of glibenclamide in said single solid oral dosage form are ±10% of said $C_{max}$ and AUC values, respectively, of glibenclamide in said separate glibenclamide solid oral dosage form.*

*25. A composition of claim 13 wherein said $C_{max}$ and AUC values of glibenclamide in said single solid oral dosage form are ±5% of said $C_{max}$ and AUC values, respectively, of glibenclamide in said separate glibenclamide solid oral dosage form.*

*26. A composition of one of claims 14 or 15 wherein said $C_{max}$ and AUC values are ±20% of said numerical ranges.*

*27. A composition of one of claims 14 or 15 wherein said $C_{max}$ and AUC values are ±15% of said numerical ranges.*

*28. A composition of one of claims 14 or 15 wherein said $C_{max}$ and AUC values are ±10% of said numerical ranges.*

*29. A composition of one of claims 14 or 15 wherein said $C_{max}$ and AUC values are ±5% of said numerical ranges.*

*30. A method of treating non-insulin dependent diabetes or hyperglycemia comprising administering to a patient in need thereof a composition of one of claims 11–15.*

*31. A method of achieving a bioavailability of glibenclamide in a human upon administering orally a single solid oral dosage form containing an effective dose of metformin and an effective dose of glibenclamide, said bioavailability being comparable to the bioavailability of glibenclamide achieved by oral administration of separate solid oral dosage forms to a human, one containing glibenclamide and the other metformin, in the same respective effective doses as in said single oral dosage form, comprising formulating glibenclamide with metformin in said single solid oral dosage form so as to assure said comparable bioavailability.*

*32. A method of increasing bioavailability of glibenclamide in a human upon administering orally a single solid oral dosage form containing an effective dose of metformin and an effective dose of glibenclamide, such that said increased bioavailability is comparable to the bioavailability of glibenclamide achieved by oral administration of separate solid oral dosage forms to a human, one containing glibenclamide and the other metformin, in the same respective effective doses as in said single oral dosage form, comprising formulating glibenclamide with metformin in said single solid oral dosage form so as to assure said comparable bioavailability.*

*33. A composition of one of claims 11–15 wherein metformin is present as a metformin salt.*

*34. A method of one of claims 31–32 wherein metformin is present as a metformin salt.*

*35. A method of claim 30 wherein metformin is present as a metformin salt.*

* * * * *

UNITED STATES PATENT AND TRADEMARK OFFICE

CERTIFICATE OF CORRECTION

PATENT NO. : RE 38,629 E
DATED : October 19, 2004
INVENTOR(S) : Yves Bonhomme et al.

It is certified that error appears in the above-identified patent and that said Letters Patent is hereby corrected as shown below:

Title page,
Item [73], Assignee, reads “Lyons” should read -- Lyon --.

Column 7,
Line 57, reads “hyperglycaemia” should read -- hyperglycemia --.

Column 8,
Line 34, reads “dose glibenclamide” should read -- dose of glibenclamide --.
Line 46, reads “about 200” should read -- about 200/1 --.

Signed and Sealed this

Eighteenth Day of October, 2005

JON W. DUDAS
*Director of the United States Patent and Trademark Office*